United States Patent [19]
Sardella

[11] Patent Number: 6,033,428
[45] Date of Patent: Mar. 7, 2000

[54] LAPAROSCOPIC SURGERY DEVICE

[76] Inventor: William V. Sardella, 9 Sugar Hollow La., West Simsbury, Conn. 06092

[21] Appl. No.: 09/237,480
[22] Filed: Jan. 26, 1999
[51] Int. Cl.$^7$ .............................. A61B 17/08; A61D 1/00
[52] U.S. Cl. ............................................................ 606/213
[58] Field of Search .................................. 606/213, 215, 606/192, 191; 604/237, 167

[56] References Cited

U.S. PATENT DOCUMENTS

| | | | |
|---|---|---|---|
| 5,526,536 | 6/1996 | Cartmill . | |
| 5,572,743 | 11/1996 | Yavitz . | |
| 5,636,645 | 6/1997 | Ou . | |
| 5,734,992 | 4/1998 | Ross . | |
| 5,853,395 | 12/1998 | Crook et al. | 606/213 |
| 5,906,577 | 5/1999 | Beane et al. | 606/213 |

*Primary Examiner*—Michael Buiz
*Assistant Examiner*—Vy Q. Bui
*Attorney, Agent, or Firm*—Alix, Yale & Ristas, LLP

[57] ABSTRACT

A laparoscopic surgical device including a wound protector, a sleeve, and a surgical glove. The wound protector has inner and outer inflatable cuffs joined by a protector member. The protector member has a passageway extending longitudinally therethrough. The surgical glove includes a cuff portion having an end segment and a wrist segment. The end segment is doubled over the wrist segment to form an annular cavity. The sleeve includes first and second oppositely disposed end portions having first and second openings, respectively. The first opening forms a rim which is positioned in a crevice formed between the outer surface of the outer cuff and the outer surface of the protector member. The second end portion is positioned and clamped within the annular cavity by the end segment of the surgical glove. The inner cuff is inserted through the incision and the inner and outer cuffs are positioned adjacent the patient's abdominal wall. The inner and outer cuffs are inflated, clamping the patient's abdominal wall therebetween and clamping and sealing the rim of the first opening in the crevice. The surgical glove and a portion of the sleeve may be inserted through the passageway of the wound protector into the patient's abdomen.

19 Claims, 4 Drawing Sheets

LAPAROSCOPIC SURGERY DEVICE

BACKGROUND OF THE INVENTION

This invention relates generally to surgical devices. More particularly, the present invention relates to devices utilized during laparoscopic surgery.

Many complex surgical procedures are now being performed in a laparoscopic-assisted fashion. The use of a hand-assisted surgical technique allows greater safety and facility in performing difficult operative procedures laparoscopically. Hand-assisted laparoscopy is facilitated by the use of a wound protecting device which extends through the abdominal wall via the surgical incision. The wound protecting device also seals the abdominal wound against $CO_2$ leakage during periods of intraabdominal insufflation.

Conventional devices for hand-assisted laparoscopy are cumbersome, difficult to use, and potentially unreliable. To effect a tight gas seal, the device attaches to the patient's skin by use of an adhesive which often unreliable during surgical manipulation and can cause skin irritation or even superficial chemical burns. Some conventional devices have a separate inner wound protector. These inner wound protectors are extremely difficult and cumbersome to place, requiring the surgeon and an assistant to simultaneously perform a difficult torquing motion. In addition, the inner end of the device sleeve fits underneath the surgical glove, greatly increasing the difficulty of removing or replacing the sleeve.

SUMMARY OF THE INVENTION

Briefly stated, the invention in a preferred form is a laparoscopic surgery device which allows complex laparoscopic surgical procedures to be performed using the assistance of the surgeons hand within a body cavity. Conventional laparoscopic surgery utilizes gas insufflation to expand the size of a body cavity thus providing visibility and exposure and therefore requires gas-tight seals. The present device incorporates three components; an inflatable wound protector, nonporous sleeve, and a special surgical glove which when combined in the method described provide an air-tight seal to maintain gas pressure within a body cavity during laparoscopic surgery.

A laparoscopic surgical procedure may be facilitated by making a small incision through which the inflatable wound protector is placed. The inner and outer cuffs can be inflated using $CO_2$ via an automatic insufflator which is readily available in any operating room equipped for laparoscopic surgery. When inflated, inner and outer cuffs provide a pressure seal from both sides of the abdominal wall preventing leakage of gas from the body cavity during a laparoscopic procedure. The central portion of the wound protector (between the inner and outer cuffs) may also be designed as an inflatable chamber and may be either separate or in communication with the inflatable inner and outer cuff chambers. The attachable sleeve is of tapered dimensions and has elastic cuffs on both ends to provide an effective seal when engaged with the wound protector and specially designed wrist portion of surgical glove. The wider end of the sleeve is placed over the partially inflated outer cuff with its elastic opening designed to fit snugly into a cleft along the undersurface of the outer cuff. Complete insufflation of the outer cuff now provides a gas-tight seal between outer cuff and sleeve components. The opposite narrow elastic end of the tapered sleeve is now placed over the surgeons glove and fits snugly onto a designated area of the specially designed surgical glove just above the wrist. The specially designed surgical glove has an elastic cuff which initially fits over the surgeons forearm and then folds down over the sleeve portion of the device to provide a gas-tight seal between sleeve and glove. As described, the present invention is a three component device which when used in combination allows the surgeons gloved hand to move freely about a body cavity without loss of intracorporeal (within a body cavity) gas pressure thereby facilitating a surgical procedure. The wound protector component whether inflated completely, partially, or deflated may be utilized separately to prevent wound contamination and provide exposure during non-laparoscopic portions of a surgical procedure. It could be similarly employed for conventional non-laparoscopic surgical procedures. The detachable sleeve component can be easily removed from both the wound protector and surgical glove and can be utilized as a specimen bag if desired. In addition, an attachable dome may be provided to fit snugly over the outer tube of the wound protector providing a gas-tight seal to allow portions of a surgical procedure to be performed in a purely laparoscopic (non hand-assisted) fashion.

It is an object of the invention to provide a new and improved laparoscopic surgery device.

It is also an object of the invention to provide a new and improved laparoscopic surgery device that provides flexibility of use combined with simplicity of design.

Other objects and advantages of the invention will become apparent from the drawings and specification.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

Figure 2:
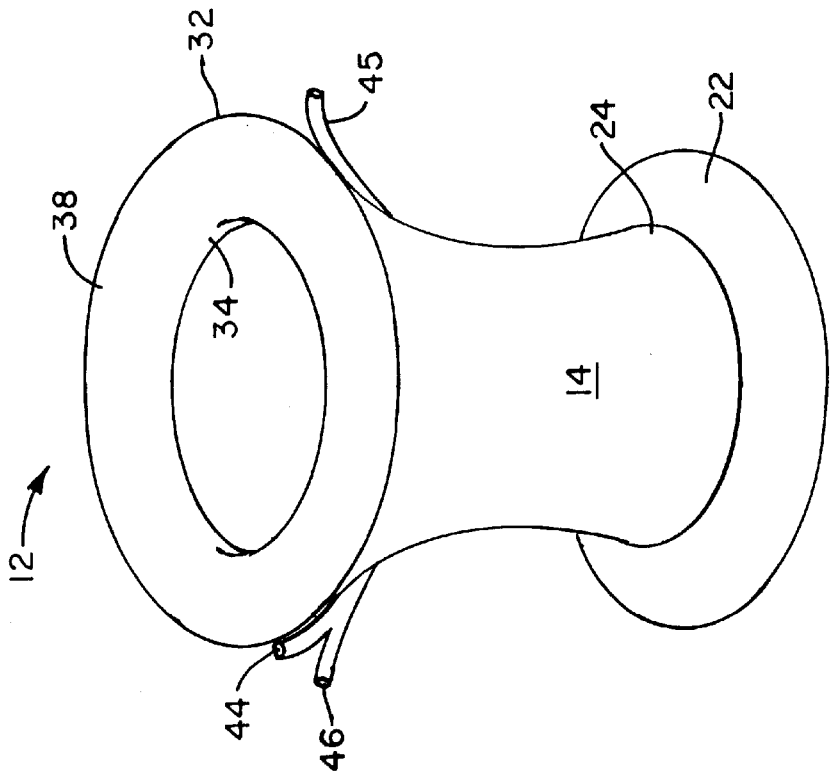
FIG. 2 is an enlarged perspective view of the wound protector of FIG. 1.

With reference to the drawings wherein like numerals represent like parts throughout the several figures, a laparoscopic surgery device in accordance with the present invention is generally designated by the numeral 10. The laparoscopic surgery device 10 includes a wound protector 12 having a protector member 14 which extends through the abdominal wall 16 via the surgical incision 18. The protector member 14 holds the incision 18 in an open position and protects the abdominal wall 16 from additional injury due to trauma, such as abrasion, during the surgical procedure.

Figure 3:
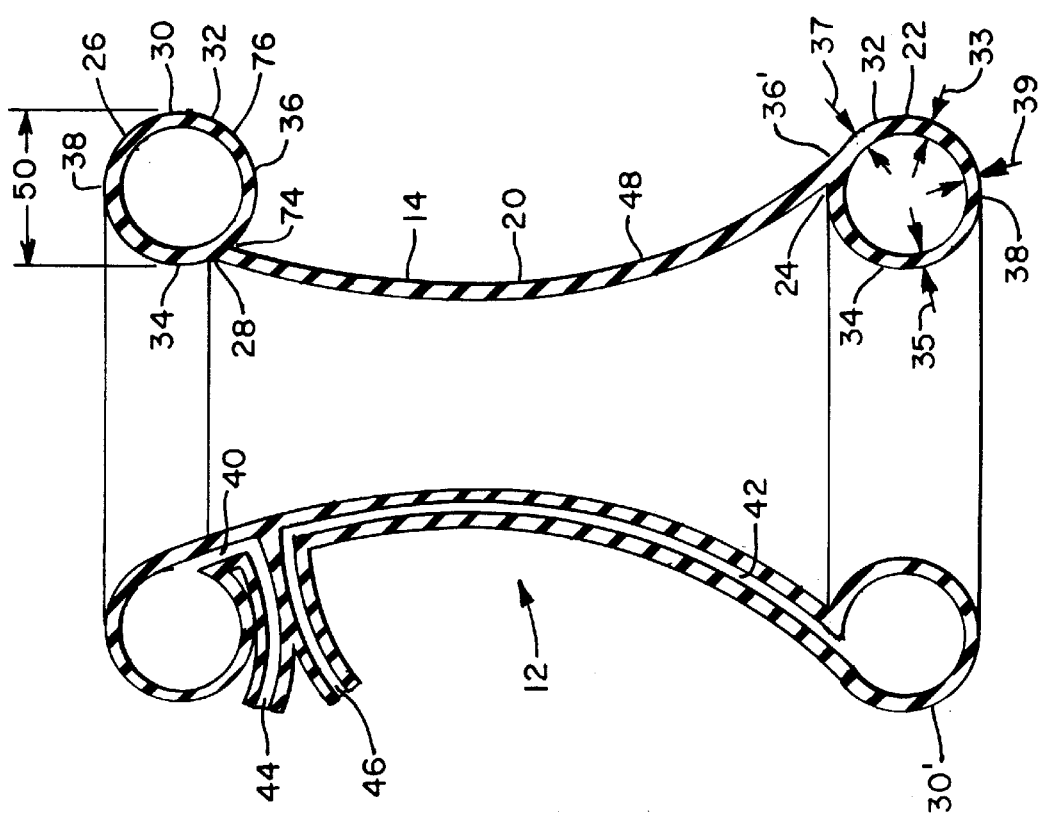
FIG. 3 is a cross-section view, taken along line 3—3 of FIG. 2.
Figure 8:
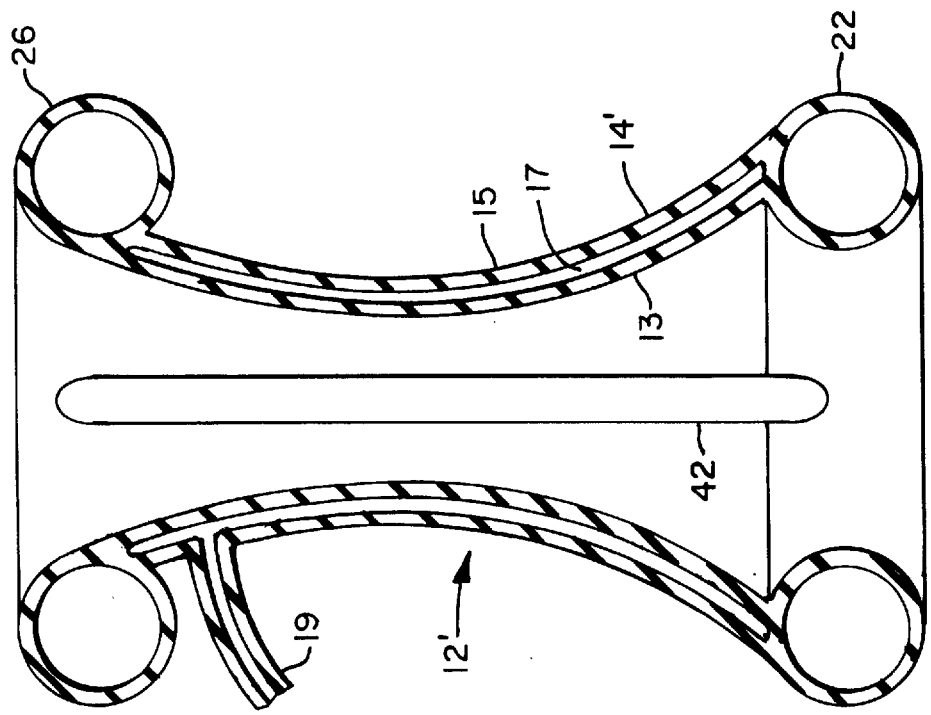
FIG. 8 is a cross-section view of an alternate embodiment of the wound protector of FIG. 3.

In a preferred embodiment (FIGS. 2 and 3), the protector member 14 is a longitudinally extending sleeve having a single wall 20 composed of a relatively thick elastic material such as latex or a suitable non-latex material. Alternatively, the protector member 14' may have inner and outer walls 13, 15 defining an annular cavity 17 which may be filled via inlet/outlet line 19 with $CO_2$ to provide a more rigid member 14' (FIG. 8). The protector member 14 is anchored within the surgical incision 18 by a circular inner cuff 22 which is mounted to the inner end 24 of the protector member 14 and a circular outer cuff 26 which is mounted to the outer end 28 of the protector member 14. The inner cuff 22 is inserted into the abdominal cavity via the surgical incision 18 and the outer cuff 26 is positioned around the incision against the skin of the abdomen. The inner and outer cuffs 22, 26 are inflated with $CO_2$, as described below, to apply a biasing force that tightens the protector member 14 against the sides of the incision 18, thereby sealing the incision 18. To ensure that the protector member 14 is properly tightened, the laparoscopic surgery device 10 is provided in "small", "medium" and "large" sizes, depending on the length of the protector member 14. The length of the protector members 14 are 5.0 cm, 7.5 cm, and 10.0 cm for the small, medium, and large devices, respectively. Preferably, the protector member 14 has an inside diameter of 8.0 cm.

The inner and outer cuffs 22, 26 are composed of an elastic material and have the shape of an inner-tube, having a substantially circular shape when viewed in cross-section. Each cuff 22, 26 has an integral wall 30', 30 comprising a circular outer wall portion 32 which is integrally joined to a coaxial, circular inner wall portion 34 by an engagement wall portion 36', 36, which abuts the outer or inner abdominal wall, and a distal wall portion 38, which is disposed oppositely to the engagement wall portion 36', 36. The inner, outer and distal wall portions 34, 32, 38 have a wall thickness 35, 33, 39 which is greater than the wall thickness 37 of the engagement wall portion 36, 36'. In one preferred embodiment, the thickness 35, 39 of the inner and distal wall portions 34, 38 is substantially equal to 1.0 mm, the thickness 33 of the outer wall portion 32 is substantially equal to 0.75 mm and the thickness 37 of the engagement wall portion 36, 36' is substantially equal to 0.5 mm. Upper and lower passageways 40, 42 connect upper and lower inlet/outlet lines 44, 46 with the outer and inner cuffs 26, 22, respectively, to provide a means of inflating or deflating the cuffs 26, 22 with $CO_2$. Since the thinner engagement wall portion 36, 36' is less able to resist the pressure exerted by the $CO_2$, the engagement wall portion 36, 36' expands outwardly to engage the abdomen upon inflation of either cuff 22, 26. The outer and inner cuffs 26, 22 exert a force on the abdomen biasing the outer and inner ends 28, 24 of the protector member 14 away from the abdominal wall 16. This biasing force forces the protector member 14 to shift from the arcuate shape shown in FIGS. 1, 2 and 3 to a straighter shape, thereby tightening the protector member 14. Consequently, the outer surface 48 of the protector member 14 intimately engages the incision surface and forces the incision walls away from each other, opening the incision 18. In a preferred embodiment, the distance 50 between the inner and outer wall portions 34, 32 is substantially equal to 3.0 cm to spread the force exerted by the engagement wall portion 36, 36' over a larger surface area of the abdomen.

Figure 4:
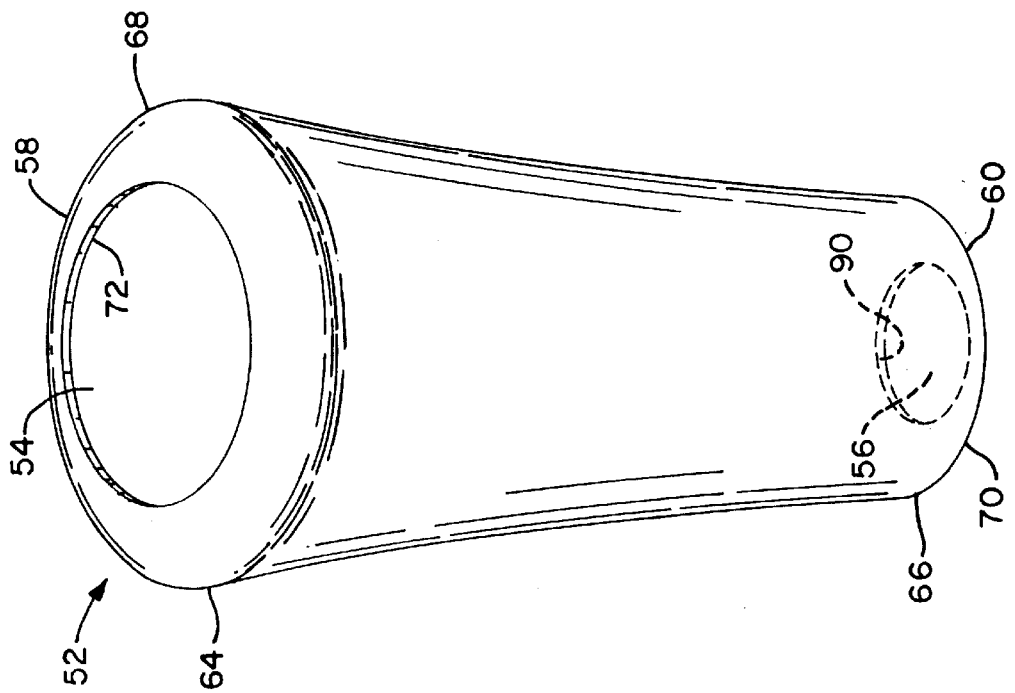
FIG. 4 is an enlarged perspective view of the sleeve of FIG. 1.

With reference to FIG. 4, a sleeve 52, composed of a nonporous flexible material such as plastic or silastic, has openings 54, 56 in the oppositely disposed protector and glove ends 58, 60. Preferably, opening 54 has an internal diameter substantially of 6.0 cm and opening 56 has an internal diameter of 5.0 cm. The openings 54, 56 are elastically stretchable to facilitate installation of the sleeve 52 on the wound protector 12 and a surgical glove 62. The sleeve 52 tapers longitudinally from a first position 64 adjacent the protector end 58 to a second position 66 adjacent the glove end 60. Preferably, the diameter of the sleeve 52 at the first position 64 is 11.0 cm and the diameter of the sleeve 52 at the second position 66 is 8.75 cm. Since the diameter of the protector and glove end openings 54, 56 is smaller than the diameter of the sleeve 52 at the first and second positions 64, 66, protector end and glove end transition portions 68, 70 are formed that extend from the first and second positions 64, 66 to the protector and glove end openings 54, 56, respectively.

Figure 6:
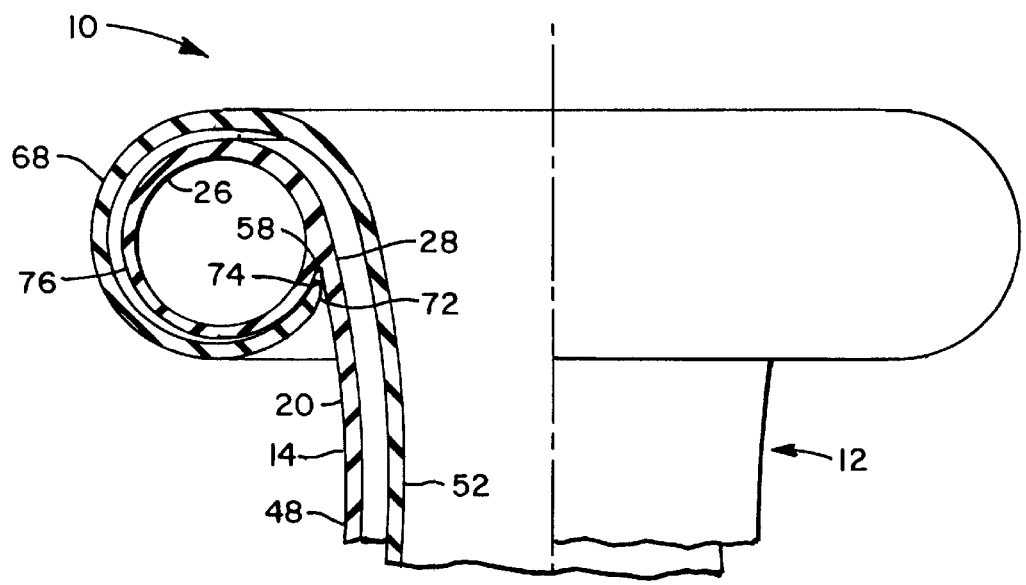
FIG. 6 is an enlarged side view, partly broken away and partly in cross-section, of the wound protector and sleeve of FIG. 1.

With reference to FIG. 6, the protector end opening 54 of the sleeve 52 may be stretched to a 10.0 cm opening to insert the sleeve 52 around the partially inflated outer cuff 26. The rim 72 of the protector end opening 54 is positioned in a crevice 74 formed between the outer surface 76 of the outer cuff 26 and the outer surface 48 of the protector member 14. When the outer cuff 26 is fully inflated, the expansion of the engagement wall portion 36 clamps the rim 72 of the protector end opening 54 between the outer cuff 26 and the protector member 14 and seals the sleeve 52 to the wound protector 12. The sleeve 52 is inserted through the wound protector 12, glove end first, such that the outer cuff 26 is disposed substantially within the protector end transition portion 68 of the sleeve 52.

Figure 1:
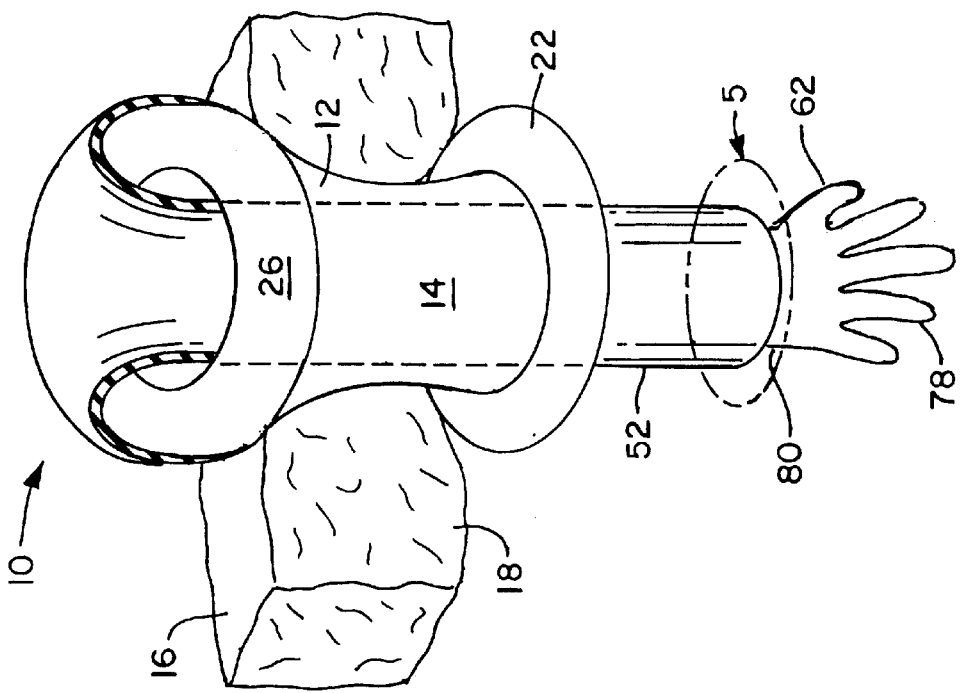
FIG. 1 is a perspective view, party in phantom and partly in cross-section, of a laparoscopic surgical device in accordance with the invention inserted through an abdominal incision.
Figure 5:
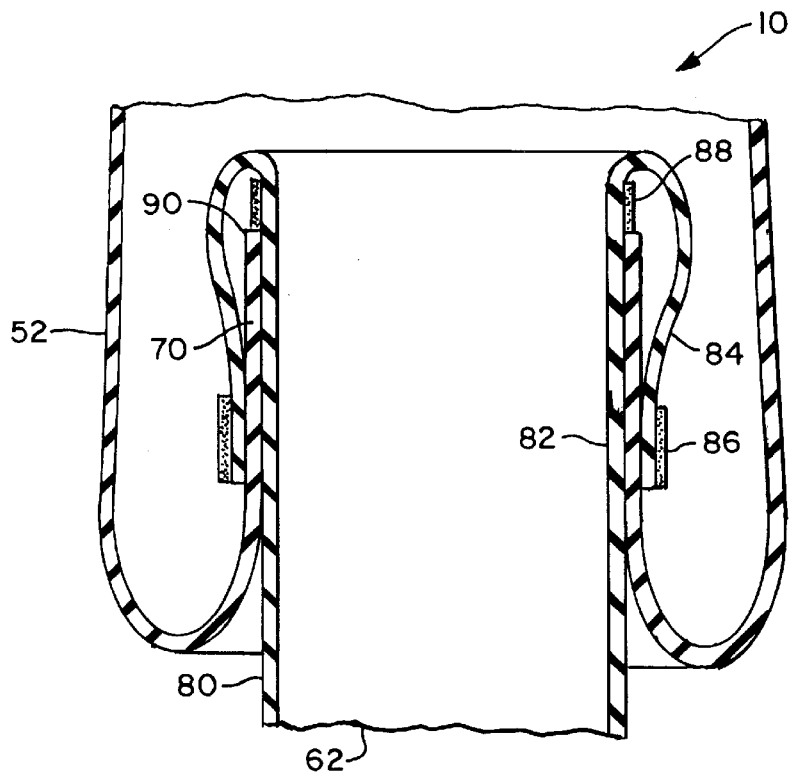
FIG. 5 is an enlarged cross-section view, partly broken away and partly in phantom, of area 5 of FIG. 1.

With reference to FIGS. 1 and 5, the surgical glove 62 has a glove portion 78 and a cuff portion 80 comprising an elongated wrist segment 82 and a cuff or end segment 84. In a preferred embodiment, a first elastic strip 86 is attached to end segment 84 and a second elastic strip 88 is attached to the wrist segment 82. Alternatively, the material characteristics of the cuff portion 80 of the surgical glove 62 may be selected such that the end segment 84 and wrist segment 82 act as the elastic strips described below. The second elastic strip 88 stretches to facilitate entry of the surgeon's hand into the surgical glove 62. When the surgeon's hand is fully inserted into the surgical glove 62, the second elastic strip 88 clamps the wrist segment 82 of the surgical glove 62 to the surgeon's wrist to effect a water tight and air tight seal. The glove end opening 56 of the sleeve 52 stretches, preferably to 8.75 cm, to allow the glove portion 78 of the surgical glove 62 to be inserted through the glove end opening 56. The rim 90 of the glove end opening 56 engages wrist segment 82 and the first elastic strip 86 stretches to allow end segment 84 to be doubled over the wrist segment 82, forming an annular cavity in which the glove end transition portion 70 of the sleeve 52 is disposed. The first elastic strip 86 clamps the glove end transition portion 70 of the sleeve 52 between the end segment 84 and the wrist segment 82, forming a water tight and air tight seal. Since the sleeve 52 does not extend past the wrist segment 82 of the surgical glove 62, sleeve material cannot interfere with the surgical procedure and the device 10 maintains the normal relationship and feel between the surgeon's hand and the surgical glove 62.

Using the outer cuff 26 to clamp the protector end 58 of the sleeve 52 in place allows the sleeve 52 to be easily installed or removed. For example, the outer cuff 26 may be partially deflated, removing the clamping force that holds the protector end 58 of the sleeve 52 in place, and the sleeve 52 withdrawn from the abdomen through the wound protector 12 to remove the sleeve 52. A new sleeve 52 is installed by inserting the protector end 58 of the new sleeve 52 into the crevice 74, reinflating the outer cuff 26, and inserting the new sleeve 52 into the abdomen via the wound protector 12. The surgical glove 62 need not be removed from the sleeve 52 before the sleeve 52 is withdrawn through the wound protector 12. Consequently, a surgical specimen may be brought through the wound protector 12 and into the everted sleeve 52. The design of the sleeve 52 allows easy disengagement from its attachment to the partially inflated outer cuff 26 and from the wrist segment 82 of the surgical glove 62. The detached sleeve 52 can now be utilized as a specimen bag if desired.

Figure 7:
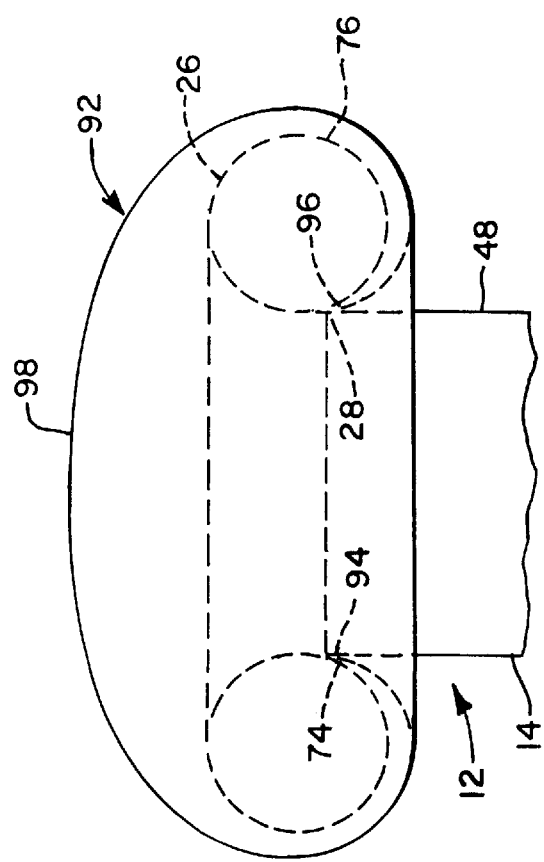
FIG. 7 is an enlarged side view, partly broken away and partly in phantom, of a detachable cover mounted on the wound protector of FIG. 1.

With reference to FIG. 7, a dome-shaped cover 92 composed of flexible material may be attached to the wound protector 12, allowing portions of the surgical procedure to be performed in a purely laparoscopic (non hand-assisted) manner. An opening 94 of the cover 92 may be stretched to a 10.0 cm opening to insert the rim 96 of the opening 94 around the partially inflated outer cuff. The rim 96 of the opening 94 is positioned in the crevice 74 formed between the outer surface 76 of the outer cuff 26 and the outer surface 48 of the protector member 14. When the outer cuff 26 is fully inflated, the expansion of the engagement wall portion 36 clamps the rim 96 of the opening 94 between the outer cuff 26 and the protector member 14 and seals the cover 92 to the wound protector 12. When the cover 92 is mounted in place, an endcap portion 98 covers the outer cuff 26 and the opening into the patients abdomen, preventing communication through the patients abdominal wall via the incision.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A laparoscopic surgical device for protecting the walls of an incision in a patient's abdominal wall and facilitating the insertion of a surgeon's hand through the incision comprising:

a wound protector having inner and outer cuffs and a protector member extending longitudinally therebetween, the protector member defining a passageway extending longitudinally therethrough, the inner and outer cuffs each defining an annular cavity and being composed of an elastic material, the protector member and the outer cuff each having an outer surface, the outer surface of the outer cuff and the outer surface of the protector member defining a crevice, the wound protector further having a first fluid passage in communication with the cavity of the inner cuff and a second fluid passage in communication with the cavity of the outer cuff; and a sleeve member having first and second oppositely disposed end portions, the first end portion defining a first opening forming a rim positioned in the crevice of the wound protector;

wherein the inner cuff is insertable through the incision, whereby the inner and outer cuffs are positioned adjacent the patient's abdominal wall and the protector member is positioned in the incision, a pressurized fluid is injectable into the cavities of the inner and outer cuffs via the first and second fluid passages wherein the inner and outer cuffs inflate to clamp the patient's abdominal wall therebetween and the outer cuff inflates to clamp and seal the rim of the first opening in the crevice, and the pressurized fluid is removable from the outer cuff via second fluid passage wherein the outer cuff deflates to unclamp the rim of the first opening whereby the sleeve member is removable from the wound protector.

2. The laparoscopic surgical device of claim 1 wherein the inner and outer cuffs each has a wall including a substantially circular inner and outer wall portions joined by an engagement wall portion disposed adjacent the protector member and a distal wall portion disposed oppositely the engagement wall portion.

3. The laparoscopic surgical device of claim 2 wherein the inner, outer, engagement, and distal wall portions of the inner and outer cuffs each have a thickness, the thickness of the engagement wall portion of each cuff being smaller than the thickness of the inner, outer and distal wall portions.

4. The laparoscopic surgical device of claim 2 wherein the inner cuff, the outer cuff, and the protector member are formed as a single, unitary structure.

5. The laparoscopic surgical device of claim 1 further comprising a surgical glove mounted to the second end portion of the sleeve member, the second end portion of the sleeve member defining a second opening providing communication with the surgical glove.

6. The laparoscopic surgical device of claim 5 wherein the first and second openings are each elastically stretchable.

7. The laparoscopic surgical device of claim 5 wherein the protector member is a tubular sleeve defining a longitudinally extending passage, the second end portion of the sleeve member and the surgical glove being insertable through the passage of the protector member into the abdomen of the patient.

8. The laparoscopic surgical device of claim 7 wherein the sleeve member further has protector end and glove end transitions portions disposed adjacent the first and second end portions, respectively, the outer cuff being disposed substantially within the protector end transition portion when the second end portion of the sleeve member is inserted through the passage of the protector member.

9. The laparoscopic surgical device of claim 8 wherein the first and second openings each have an inside diameter and the protector end and glove end transition portions each have a diameter, the diameter of at least a portion of the protector end and glove end transition portions being greater than the inside diameters of the first and second openings, respectively.

10. The laparoscopic surgical device of claim 5 wherein the surgical glove has a glove portion and a cuff portion including an end segment and a wrist segment extending between the end segment and the glove portion, at least a part of the cuff portion being elastically stretchable for clamping and sealing the surgical glove to the surgeon's hand.

11. The laparoscopic surgical device of claim 10 wherein the end segment is doubled over the wrist segment forming an annular cavity, the second end portion of the sleeve member being disposed in the annular cavity.

12. The laparoscopic surgical device of claim 11 wherein at least a portion of the end segment is elastically stretchable for clamping the second end portion of the sleeve member to the cuff portion.

13. The laparoscopic surgical device of claim 12 wherein the cuff portion further includes first and second elastic strips mounted to the end segment and wrist segment, respectively, the first elastic strip clamping the second end portion of the sleeve member to the cuff portion and the second elastic strip clamping and sealing the surgical glove to the surgeon's hand.

14. The laparoscopic surgical device of claim 1 wherein the second portion of the sleeve member comprises an endcap which covers the outer cuff and prevents communication through the patients abdominal wall via the incision.

15. The laparoscopic surgical device of claim 1 wherein the protector member comprises inner and outer walls defining an annular void therebetween and the wound protector further includes a third fluid passage in communication with the void.

16. A laparoscopic surgical device for protecting the walls of an incision in a patient's abdominal wall and facilitating the insertion of a surgeon's hand through the incision comprising:

a wound protector having inner and outer inflatable cuffs and a protector member extending longitudinally therebetween, the protector member defining a passageway extending longitudinally therethrough, the protector member and the outer cuff each having an outer surface, the outer surface of the outer cuff and the outer surface of the protector member defining a crevice;

a sleeve member having first and second oppositely disposed end portions, the first end portion defining a first opening forming a rim positioned in the crevice of the wound protector;

wherein the inner cuff is insertable through the incision, whereby the inner and outer cuffs are positioned adjacent the patient's abdominal wall and the protector member is positioned in the incision, the inner and outer cuffs are inflated to clamp the patient's abdominal wall therebetween and the outer cuff is inflated to clamp and seal the rim of the first opening in the crevice.

17. A laparoscopic surgical device for protecting the walls of an incision in a patient's abdominal wall and facilitating the insertion of a surgeon's hand through the incision comprising:

a wound protector having inner and outer inflatable cuffs and a protector member extending longitudinally therebetween, the protector member and the outer cuff each having an outer surface, the outer surface of the outer cuff and the outer surface of the protector member defining a crevice, the protector member defining a passageway extending longitudinally therethrough;

a surgical glove having a glove portion and a cuff portion including an end segment and a wrist segment extending between the end segment and the glove portion, the end segment being doubled over the wrist segment forming an annular cavity; and a sleeve having first and second oppositely disposed end portions, the first and second end portions defining first and second openings, respectively, the first opening forming a rim, the first end portion being positioned in the crevice of the wound protector and the second end portion being positioned and clamped within the annular cavity by the end segment of the surgical glove;

wherein the inner cuff is insertable through the incision, whereby the inner and outer cuffs are positioned adjacent the patient's abdominal wall and the protector member is positioned in the incision, the inner and outer cuffs are inflatable to clamp the patient's abdominal wall therebetween, the outer cuff is inflatable to clamp and seal the rim of the first opening in the crevice, and the surgical glove and a portion of the sleeve are insertable through the passageway of the wound protector into the patient's abdomen.

18. The laparoscopic surgical device of claim 17 wherein the inner and outer cuffs each include substantially circular inner and outer wall portions joined by an engagement wall portion disposed adjacent the protector member and a distal wall portion disposed oppositely the engagement wall portion, the inner, outer, engagement and distal wall portions defining an annular cavity.

19. The laparoscopic surgical device of claim 18 wherein the inner, outer, engagement, and distal wall portions of the inner and outer cuffs each have a thickness, the thickness of the engagement wall portion of each cuff being smaller than the thickness of the inner, outer and distal wall portions.

* * * * *